United States Patent
Pons et al.

(10) Patent No.: US 9,618,467 B2
(45) Date of Patent: Apr. 11, 2017

(54) METHOD OF ELECTRICALLY CHARACTERIZING A COMPOSITE MATERIAL FOR MANUFACTURING AN AIRCRAFT

(75) Inventors: Francois Pons, Toulouse (FR); Nicolas Larrose, Launaguet (FR)

(73) Assignee: Airbus Operations SAS (FR)

( * ) Notice: Subject to any disclaimer, the term of this patent is extended or adjusted under 35 U.S.C. 154(b) by 290 days.

(21) Appl. No.: 13/386,767

(22) PCT Filed: Jul. 20, 2010

(86) PCT No.: PCT/FR2010/051526
§ 371 (c)(1),
(2), (4) Date: Jan. 24, 2012

(87) PCT Pub. No.: WO2011/012794
PCT Pub. Date: Feb. 3, 2011

(65) Prior Publication Data
US 2012/0119761 A1 May 17, 2012

(30) Foreign Application Priority Data

Jul. 31, 2009 (FR) ..................................... 09 55433

(51) Int. Cl.
*G01R 27/08* (2006.01)
*G01N 27/04* (2006.01)

(52) U.S. Cl.
CPC ................................. *G01N 27/041* (2013.01)

(58) Field of Classification Search
CPC ........ G01R 27/08; G01R 31/02; G01N 27/04; G01N 3/08; G01B 7/16; G01M 5/0083; G01M 5/0016; G01M 5/0041; B29C 70/10

USPC ................................................... 324/537, 691
See application file for complete search history.

(56) References Cited

U.S. PATENT DOCUMENTS

| | | | |
|---|---|---|---|
| 3,864,155 A * | 2/1975 | Graham | 428/378 |
| 4,924,187 A | 5/1990 | Sprunt et al. | |
| 4,954,782 A * | 9/1990 | Ball | 324/538 |
| 7,607,594 B2 * | 10/2009 | Saripalli | 239/590.3 |

(Continued)

FOREIGN PATENT DOCUMENTS

| DE | 36 22 656 C1 | 10/1987 |
|---|---|---|
| DE | 102 34 172 A1 | 7/2003 |

(Continued)

OTHER PUBLICATIONS

Haug, R. et al., "An electrical method of measuring the hardness of a material," *Measurement Science and Technology*, Mar. 1991, pp. 247-252, vol. 2, No. 3 (with English-language Abstract).

(Continued)

*Primary Examiner* — Son Le
*Assistant Examiner* — Brent J Andrews
(74) *Attorney, Agent, or Firm* — Lerner, David, Littenberg, Krumholz & Mentlik, LLP

(57) ABSTRACT

In the method of electrically characterizing a composite material for manufacturing an aircraft, the following steps are performed: compressing two spacers against at least one test piece made of a composite material; determining an electrical resistance value for the assembly formed by the spacers and the test piece; and deducing from said value a value for the electrical resistance of the composite material.

8 Claims, 3 Drawing Sheets

(56) References Cited

U.S. PATENT DOCUMENTS

| | | | |
|---|---|---|---|
| 7,642,774 B2 | 1/2010 | Fleury et al. | |
| 2004/0016286 A1* | 1/2004 | Prakash | 73/9 |
| 2007/0096751 A1* | 5/2007 | Georgeson | G01R 27/2623 |
| | | | 324/691 |
| 2008/0061774 A1* | 3/2008 | Georgeson et al. | 324/240 |

FOREIGN PATENT DOCUMENTS

| | | | |
|---|---|---|---|
| DE | 10234172 A1 * | 7/2003 | G01N 3/08 |
| EP | 2 034 308 A1 | 3/2009 | |
| FR | 2 630 545 A1 | 10/1989 | |
| GB | 2 218 813 A | 11/1989 | |
| GB | 2218813 A * | 11/1989 | |
| JP | A-H09-026446 | 1/1997 | |
| JP | A-2001-318070 | 11/2001 | |
| JP | A-2002-228681 | 8/2002 | |
| RU | 2 140 071 | 10/1999 | |
| RU | 2 194 976 | 12/2002 | |
| RU | 2 363 942 | 8/2009 | |

OTHER PUBLICATIONS

International Search Report issued in International Application No. PCT/FR2010/051526 on Dec. 16, 2010 (with translation).

Feb. 16, 2013 Office Action issued in Chinese Patent Application No. 201080034080.2 (with translation).

International Preliminary Report on Patentability dated Jan. 31, 2012 issued in International Patent Application No. PCT/FR2010/051526 (with translation).

Aug. 19, 2014 Japanese Office Action issued in Application No. 2012-522214 (with translation).

Moriya, K. et al. "A Study on Flaw Detection Method for CFRP Composite Laminates (1$^{st}$ Report), The Measurement of Crack Extension in CFRP Composites by Electrical Potential Method," Journal of the Japan Society for Aeronautical and Space Sciences, vol. 36, No. 410, pp. 139-146, Mar. 1988 (with English Abstract).

* cited by examiner

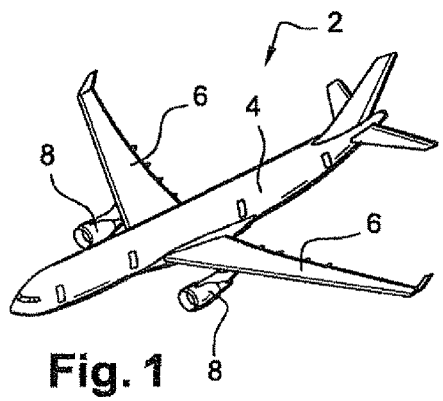
Fig. 1
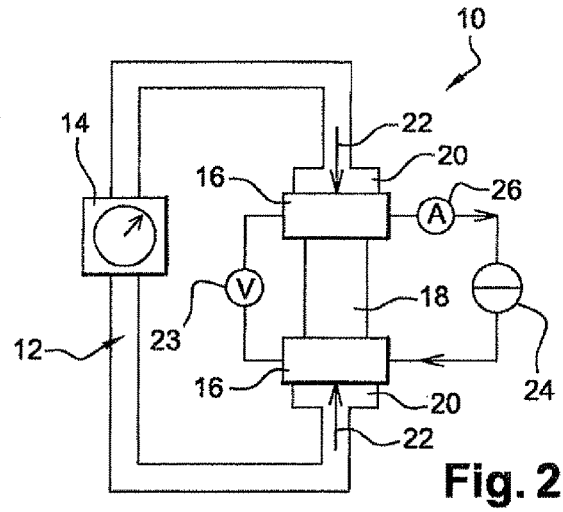
Fig. 2
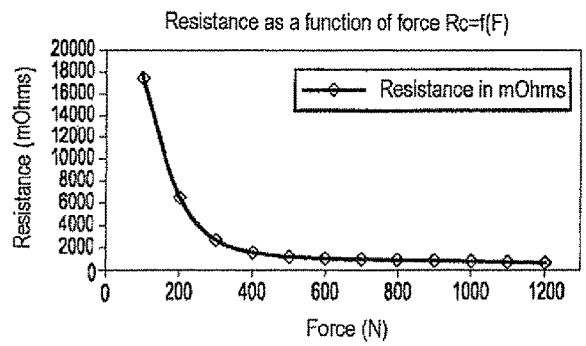
Fig. 3
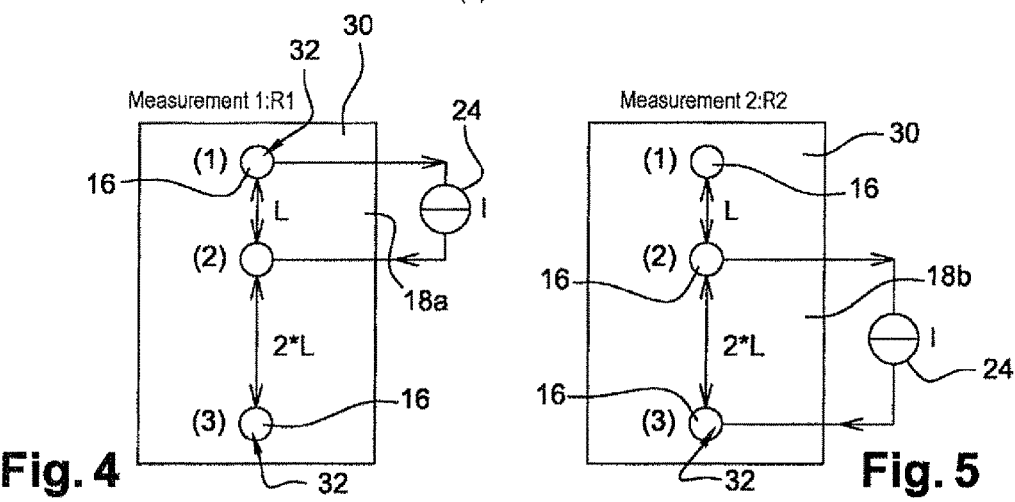
Fig. 4        Fig. 5

METHOD OF ELECTRICALLY CHARACTERIZING A COMPOSITE MATERIAL FOR MANUFACTURING AN AIRCRAFT

FIELD OF INVENTION

The invention relates to composite materials used in the manufacture of aircraft.

BACKGROUND OF THE INVENTION

Nowadays, it is desired to manufacture aircraft using composite materials, in particular because of their reduced weight and because of their mechanical properties. Such composite materials are constituted by a matrix of synthetic material, e.g. epoxy resin, having embedded therein fibers such as carbon fibers.

When such a material is to be used in building an aircraft, it is useful to know how it behaves in terms of electrical resistance. For this purpose, the following procedure is nowadays implemented. A bar of composite material is made that comprises a stack of a plurality of plies. The number of plies is known and the plies are oriented, e.g. in the sequence 450/0°/−45°/90° . . . . A metal that is a good conductor of electricity is deposited electrolytically at both ends of the bar. A voltmeter is used to measure the potential difference that exists between those two deposits while the bar is being supplied with an electric current in series via an ammeter. Knowing the voltage and the current thus makes it possible to obtain the resistance of the bar in application of Ohm's law $R=U/I$.

Nevertheless, it is found to be relatively difficult to make the electrolytic deposit at the ends of the bar. Such an operation is lengthy, onerous, and without any guarantee of reliability. In particular, the quality of the surface treatment constituted by the electrolytic deposit depends to a large extent on the care applied in preparing the bar, which in practice means that it is necessary to implement about ten different steps in order to ensure that the deposit is made correctly. These steps call on specific personnel and means, thereby causing this service itself to present a cost that is not negligible. Furthermore, it is sometimes found that the results obtained are incoherent and depend in fact on the quality of the deposit that has been made. In addition, given that current is fed to the ends of the bar and that voltage is measured by means of clips, the electrolytic deposit ages quickly, which sometimes makes the experiment difficult to repeat.

OBJECT AND SUMMARY OF THE INVENTION

An object of the invention is to make it easier for a composite material to be characterized electrically.

To this end, the invention provides a method of electrically characterizing a composite material for manufacturing an aircraft, wherein the method comprises the steps of:

compressing two spacers against at least one test piece made of a composite material;

determining an electrical resistance value for the assembly formed by the spacers and the test piece; and deducing from said value a value for the electrical resistance of the composite material.

Thus, the electrolytic deposit is replaced by establishing a contact pressure between the spacers and the test piece. Contact between each spacer and the test piece does indeed give rise to electrical contact resistance. Nevertheless, this magnitude can be controlled or eliminated at will by calculation so that this method of operation makes it possible to obtain an electrical resistance value for the composite material in a manner that is reliable. The method is also easier and quicker to implement than the method associated with making an electrolytic deposit. It provides results that are reliable and the measurements are reproducible.

Advantageously, the compression is performed in such a manner that the or each test piece is subjected to a contact pressure exceeding a predetermined threshold.

It has been found, surprisingly, that when the compression force to which the test piece is subjected between the spacers is increased, the electrical resistance of the assembly drops quickly and then tends towards an asymptote. This shows that the electrical contact resistance between each spacer and the test piece remains substantially constant once the pressure has exceeded the threshold, and it may even become a magnitude that is negligible. Thus, the existence of electrical contact resistance does not constitute an obstacle to characterizing the resistance of the composite material itself.

Advantageously, at least one of the spacers is inserted in an orifice in the or each test piece, and a tight fit is established between the spacer and the orifice.

This constitutes an assembly technique that is simple and convenient and that serves to reduce the electrical contact resistance between each spacer and the test piece.

Advantageously, the spacer presents a diameter that is greater than the diameter of the orifice.

Preferably, the diameter c of the spacer and the diameter e of the orifice satisfy the following equation:

$$(c-e)/c \geq 0.0025$$

Thus, the electrical contact resistance between each spacer and the test piece becomes negligible.

Preferably, compression is performed on at least two test pieces made of the same composite material.

By combining the results obtained using the test pieces, this makes it possible to eliminate calculating the electrical contact resistance, and thus avoids any need for this parameter to be taken into account.

Advantageously, compression is performed in succession on the two test pieces while keeping the location of one of the spacers unchanged.

This reduces the amount of manipulation. Furthermore, by reducing the number of breaks in contact between the spacers and the test pieces, the reliability of the results is improved.

Preferably, the two test pieces form portions of a single part.

This serves to reduce any risk in the property differing between the two test pieces, thereby improving the reliability of the results.

Preferably, three spacers are arranged on the part at locations that are mutually in alignment.

By means of calculations that are particularly simple, this method makes it possible to obtain an electrical resistance value for the material.

The invention also provides a computer program including code instructions that make it suitable for controlling the implementation of at least some of the steps of the method of the invention, when executed on a computer.

The invention also provides a data recording medium, including such a program in recorded form.

The invention also provides making such a program available on a telecommunications network for downloading.

The invention also provides a method of manufacturing an aircraft in which the aircraft is manufactured using a composite material that has been electrically characterized by means of the method of the invention, with the electrical resistance value of the material as obtained by the method being taken into account.

Preferably, electrical equipment of the aircraft is connected to a part made of the composite material, and the aircraft is arranged in such a manner that a fault current circuit for the equipment passes via the part.

The invention also provides an installation for electrically characterizing a composite material for use in manufacturing an aircraft, wherein the installation comprises:

at least two spacers;

means for compressing the two spacers against a test piece; and means for determining an electrical resistance value for the assembly constituted by the spacers and the test piece.

The invention also provides an aircraft manufactured by means of a composite material that has been electrically characterized by means of a method of the invention.

The aircraft preferably includes electrical equipment that is connected to the part and that is arranged in such a manner that a fault current circuit for the equipment passes via the part.

The invention may be applied for example in the following context.

An aircraft includes a very large number of pieces of electrical equipment or apparatus of various kinds. They may be motors or indeed electronic devices such as computers.

Among such pieces of equipment, many are electrically powered with a single phase. For this purpose, the equipment is connected to the positive terminal of the generator by means of a cable. As for the connection to the negative terminal generator, this takes place by connecting the other terminal of the equipment to the metal ground of the airplane which also has a negative terminal of the generator connected thereto. That constitutes the circuit for operating currents.

It is also necessary to make provision for carrying possible fault currents relating to the equipment. By way of example, this type of current may be a leakage current or a short circuit current and it may appear in the event of an anomaly. When the airplane is made mostly out of metal, fault currents can be carried in the same way as operating currents, with the equipment being connected to metal parts of the airplane.

However things are different when it is desired to make a portion of the airplane out of composite material comprising a plastics material matrix reinforced by non-metallic fibers. Such a material is a less good conductor of electricity than is metal.

In order to connect the metal ground of the aircraft to the pieces of equipment present in an aircraft of this type so as to carry operating currents, each piece of equipment is connected to said ground by means of a specific cable. It is thus known to envisage a specific metal network that, in the fuselage, is sometimes referred to as being the electrical structure network or "ESN".

Furthermore, provision must be made for a possible fault current from the equipment to return to metal ground. For this purpose, a specific fault network is used that is referred to as the metallic bonding network or "MBN". This network coincides in part with structural metal parts of the airplane such as seat rails in order to provide the airplane with a mesh or lattice capable of carrying fault currents from equipment. In this context, it is known to provide specific components such as metal tapes on each frame and each cross-member of the airplane so as to provide electrical continuity between the metal parts of the airplane in spite of the presence of the composite material, which continuity serves to carry fault currents to the ground of the airplane.

However, together these metal elements can form a mesh that is complex and that gives rise to numerous problems. Thus, adding specific components increases the weight of the airplane. It increases the length of time needed for accomplishing all assembly operations. The associated cost is not negligible. These elements also make the current return network more complex. Such elements require special studies to be made relating to dimensioning, to maintenance, to corrosion, and to interconnecting different portions of the ESN.

That is why, advantageously, the invention provides an aircraft including at least one piece of electrical equipment and a composite material part to which the equipment is connected, with the composite material having been characterized by means of the invention, the aircraft being arranged in such a manner that a fault current circuit for the equipment passes via the part.

Thus, any fault currents from the equipment can be carried by means of a non-uniform network made up both of composite material and of metal. The metal portion of the network corresponds to the metal ground of the aircraft. This is the main network. The part(s) made of composite material then form(s) a delivery network enabling fault currents to be directed to this main network. It is thus the composite material parts themselves that are used for carrying fault currents from the equipment. Advantage is taken of the fact that the electrical properties of composite materials on board aircraft do not enable them to carry to ground the operating currents of the aircraft, but in contrast do enable them to carry fault currents. Implementation does not require a large number of specific components to be added. It does not give rise to extra weight nor does it significantly increase the length of time required for assembly operations. There is no significant extra cost, and the electric current return network is not made more complicated. Finally, there is no need to provide for the above-mentioned studies for interconnecting the various portions of the ESN. The composite material has been characterized as stated above for enabling use thereof in this application.

Advantageously, the aircraft includes at least one contact member connected to the equipment and assembled to the part by means of a tight fit between the member and the part.

This ensures good connection between the equipment and the composite material part so as to enable fault currents to be carried appropriately. More precisely, this tight fit serves to make the contact resistance between the member and the part minimal or even negligible, thereby making it easier to carry fault currents via the composite material part.

Preferably, the contact member extends in an orifice of the part, the diameter v of the member and the diameter e of the part satisfying the following equation:

$$(v-e)/v \geq 0.0025$$

This relationship between the diameters ensures that the contact resistance is negligible.

Advantageously, the composite material comprises a plastics material reinforced by carbon fibers.

Preferably, a majority of the length of the fault current circuit comprises parts of the aircraft that are made of metal.

Thus, the network is made up for the most part out of metal elements, in particular structural elements of the airplane, thereby obtaining the lowest possible mesh electrical resistance.

Advantageously, the numbers of pieces of electrical equipment and the numbers of composite material parts are at least two, the aircraft including a metal structure connected to the composite material part such that the fault current circuit of each piece of equipment passes via the associated part and the metal structure without passing via the part associated with each other piece of equipment.

Preferably, the aircraft includes a monitoring device suitable for detecting a fault current relating to the equipment.

This device serves to protect the equipment from the possible consequences of a fault current appearing.

Preferably, the device is suitable for interrupting an electrical power supply to the equipment on detecting a fault current relating to the equipment.

Advantageously, the monitoring device forms part of the equipment.

The device is thus dedicated to the equipment. In the event of fault current, it is capable of isolating the equipment without interrupting the operation of other pieces of equipment. It does not require a specific assembly operation to be performed on the aircraft assembly line.

Advantageously, in the aforesaid method of the invention, a piece of electrical equipment of the aircraft is connected to a part formed by the composite material characterized by means of the invention, and the aircraft is arranged in such a manner that a fault current circuit for the equipment passes via the part.

Preferably, at least one contact member is connected to the equipment and the contact member is assembled with the part by means of a tight fit between the member and the part.

BRIEF DESCRIPTION OF THE DRAWINGS

Other characteristics and advantages of the invention appear further from the following description of an embodiment and an application given as non-limiting examples with reference to the accompanying drawings, in which:

FIG. 1 is a perspective view of an airplane made out of a composite material that is characterized by the method of the invention;

FIG. 2 is a diagram of a characterization installation of the invention;

FIG. 3 is a graph plotting a curve showing how the resistance of the stack in the FIG. 2 installation varies as a function of the force exerted on said stack;

FIGS. 4 and 5 show two steps in an implementation of the method of the invention;

MORE DETAILED DESCRIPTION

Figure 6:
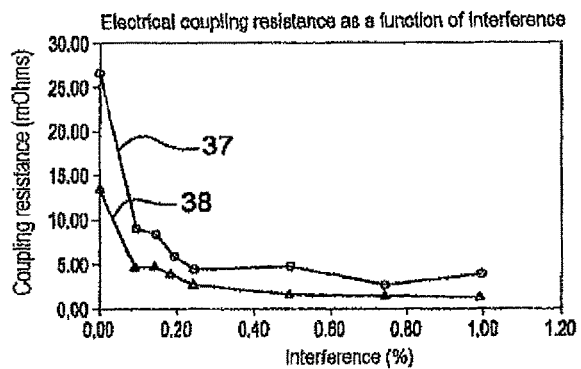
FIG. 6 is a graph plotting curves showing how the coupling resistance varies as a function of interference in the setups of FIGS. 4 and 5.

FIG. 1 shows an aircraft 2, here constituted by an aerodyne, specifically forming an airplane. The airplane has a fuselage 4, two wings 6, and two engines 8 carried by the wings in the present example.

At least certain portions of the airplane, such as the fuselage 4 or the wings 6 are made by means of at least one composite material, amongst other materials.

Such a material in the present example comprises a plastics material such as an epoxy resin forming a matrix having fibers embedded therein, specifically such as carbon fibers in this example. This is a material of the carbon fiber reinforced plastic (CFRP) type.

There follows a description of an implementation of the method of the invention for electrically characterizing such a composite material, with this being done by means of the installation 10 shown in FIG. 2. The installation comprises a compression machine 12 such as a press. In particular, the machine comprises two plates 20 between which the compression force is exerted, and a screen or dial 14 serving to indicate the compression force being exerted. The installation includes two spacers 16 made of a metal that is a good conductor of electricity. It is preferable to use a ductile metal, i.e. a metal that is relatively easy to deform.

In the method of the invention, use is made of a test piece 18 made of a composite material, e.g. in the form of a section element of section that is rectangular or circular. By way of example, it may be a bar of composite material made up of an assembly of a plurality of plies e.g. oriented in the sequence 45/0°/−45/90° . . . .

A stack is made by placing the test piece 18 so that it is sandwiched between the two spacers 16 that are situated at the longitudinal ends of the test piece. The assembly is placed between two plates 20 of the machine 12 so that the plates exert two forces 22 in opposite directions on the spacers 16, these forces being directed along the direction of the stack, i.e. from one of the spacers to the other.

The installation 10 also includes means for measuring a potential difference across the terminals of the stack, these means comprising, by way of example, a voltmeter 23 connected to the two respective spacers 16. The installation also includes an electricity generator 24 suitable for feeding electricity to the stack via the two spacers. Means for measuring the current, such as an ammeter 26, are connected in series in the circuit.

By means of this installation, the test piece 18 is compressed between the two spacers 16. The dial 14 conveys the magnitude of the force 22 exerted on the stack. On the basis of the measured voltage and current obtained from the voltmeter and the ammeter, Ohm's law applies at all times to give the overall resistance of the stack formed by the two spacers and the test piece.

The results given in the following table have been obtained experimentally in this way, which table gives in its two columns, respectively the compression force 22 in newtons (N) and the measured resistance in milliohms (mΩ):

| Compression force in N | Resistance measured in mΩ |
|---|---|
| 100 | 17500 |
| 200 | 6700 |
| 300 | 2900 |
| 400 | 1770 |
| 500 | 1410 |
| 600 | 1210 |
| 700 | 1060 |
| 800 | 944 |
| 900 | 845 |

-continued

| Compression force in N | Resistance measured in mΩ |
|---|---|
| 1000 | 766 |
| 1100 | 706 |
| 1200 | 659 |

This data is plotted by the curve in FIG. 3 which plots variation in resistance in mΩ up the ordinate axis as a function of the exerted force along the abscissa axis. It can be seen that the resistance drops suddenly down to about a force of 400 N and thereafter tends asymptotically towards the value of 600 Ohms (Ω).

By way of example, it is possible to calculate the contact pressure as obtained in this way for a force 22 of 1000 N. The section of the test piece in this example is S=123.41 square millimeters (mm²), so the contact pressure is obtained as follows:

$$\epsilon = F/S = 1000/123.41 = 8 \text{ megapascals (MPa)}$$

If it is assumed that the electrical resistance of the spacers 16 is negligible, the overall resistance R as measured in this way satisfies:

$$R = 2 \ast R_C + R_{CFRP} \ast L$$

R is the overall electrical resistance of the stack as obtained from the measurements;

$R_C$ is the electrical contact resistance between the test piece and each of the spacers 16;

$R_{CFRP}$ is the electrical resistance per unit length of the material of the test piece; and L is the length of the test piece.

Naturally, the greater the exerted force, the greater the contact pressure. The curve of FIG. 3 shows that starting from a compression force threshold, e.g. set to 400 N in the present example, the electrical contact resistance $R_C$ may be considered as being constant, i.e. as being quantity that is negligible. It follows that, starting from this threshold, it is possible to consider that the value of the contact resistance is minimized and under control, thus making it possible to electrically characterize the composite material 18 itself.

This characterization may be performed in numerous ways. One such way is described below as an example. With reference to FIGS. 4 and 5, two test pieces 18*a* and 18*b* are used that, in this example, are formed as a single piece on a common part 30 made of the composite material to be characterized. This part is in the form of a rectangular block. The part presents locations 32 for receiving spacers 16. Specifically, these locations are in the form of bores or housings, each being designed to receive a respective spacer 16 that is made in the form of an insert. The orifices are cylindrical in shape and of circular section, as are the spacers 16 in the present example. The orifices have mutually parallel axes and they all open out into the same face of the part. The bores are identical in shape and in dimensions. Specifically, the housings 32 are three in number in the part 30. They are in alignment and arranged in such a manner that the distance L between the first and second housings 32 is half the distance 2L between the second and third housings.

It is desired to ensure that each of the test pieces 18*a*, 18*b* is subjected to a contact pressure that exceeds a predetermined threshold. To do this, the orifices and the spacers are dimensioned so as to achieve a tight fit between each spacer and its bore. In other words, so-called "interference" fastening is implemented. Specifically, the spacer presents a diameter c that is greater than the diameter e of the bore, with these diameters satisfying the following relationship:

$$(c-e)/c \geq 0.0025$$

The value of 0.0025 serves to ensure that the contact resistance is negligible. Even better results can be obtained if the contact resistance is further reduced, e.g. by taking a minimum value equal to 0.0030 or even 0.0035. Naturally, it is preferable in contrast to limit the ratio (c–e)/c so that it does not exceed 0.0083, for example, so as to avoid exceeding the strength capacity of the plastics material.

FIG. 6 plots two experimental curves showing how the coupling resistance, or contact resistance, plotted up the ordinate axis varies as a function of the assembly clamping between the spacer or insert and the bore that receives it. This is the magnitude (c–e)/c referred to by the term "interference", and measured as a percentage, that is plotted along the abscissa axis. The upper curve 37 shows the results of tests on a thermoplastic material, while the lower curve 38 relates to a thermoplastic material. It can be seen that from an interference value of 0.25%, the coupling resistance remains less than 5 mΩ with both materials.

The method of the invention is implemented as follows.

Two spacers 16 are inserted in the first and second orifices 32. Since the fit is a tight fit, this is done with the help of a tool such as a press. Via the male-female assemblies made in this way, a compression force is exerted on the test piece extending between the two spacers, between the two housings in the direction corresponding to the length L. It can thus be seen that radial pressure is applied between each spacer and the test piece so as to obtain contact pressure between the spacer and the bore of the composite material. The above-mentioned choice for the diameters enables the pressure to exceed 100 MPa. The installation 10 thus exerts a pressure such that the force obtained exceeds the predetermined threshold for making the contact resistance substantially constant and minimal.

As above, an electric current is caused to pass between the two spacers 16, which current is measured as is the potential difference between the two spacers, thus obtaining a resistance value $R_1$ for the assembly formed by the two spacers and the portion 18*a* forming the first test piece of the part 30.

With reference to FIG. 5, in a subsequent step, the same operations are performed, this time inserting the spacers 16 in the second and third housings 32. The measured current and potential difference serves to obtain a resistance value $R_2$ for the assembly comprising the two spacers 16 and the test piece 18*b* forming the portion of the part that extends between the two corresponding housings.

The following system of two equations is thus obtained:

$$R_1 = 2 \ast R_C + R_{CFRP} \ast L$$

$$R_2 = 2 \ast R_C + R_{CFRP} \ast 2L$$

$R_1$ and $R_2$: are the measured electrical resistances;

$R_C$: the electrical contact resistance at each spacer;

$R_{CFPR}$: the electrical resistance per unit length of the composite material; and L: the spacing, here equal to 50 millimeters (mm).

Knowing that the pressure exerted (100 MPa) in the steps of FIGS. 4 and 5 is the same in each of the bores, the same applies for the magnitude $R_C$. It can therefore be eliminated in order to obtain the electrical resistance per unit length of the composite material. By combining these two equations, the following equation is obtained:

$$R_{CFRP} = (R_2 - R_1)/L$$

It can be seen that the spacer 16 situated in the second housing 32 may stay in place when going from the step of FIG. 4 to the step of FIG. 5, thereby making it possible to improve the reliability of the result.

One or more steps of the method of the invention may be controlled by means of a computer program having code instructions enabling these steps to be executed when the program is executed on a computer. The program may be recorded on a data recording medium or it may be available on a telecommunications network for downloading.

This principle of characterization may for example be applied as follows.

Figure 8:
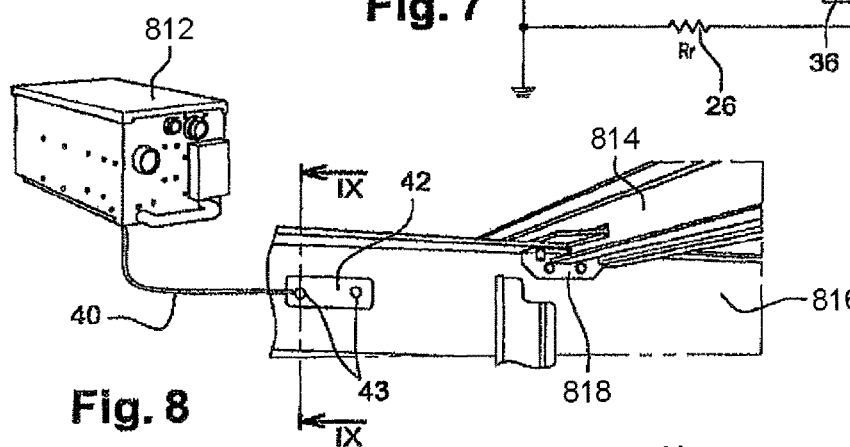
FIG. 8 is a view of the equipment and of its connection to a portion of the structure of the FIG. 1 airplane.

The airplane 2 has numerous pieces of electrical equipment on board constituted by various devices and appliances. By way of example, these may be motors or electronic devices such as computers. One of these pieces of equipment 812 is shown in FIG. 8. The structure of the airplane comprises structural parts made of metal such as the seat rail 814 shown in FIG. 8. The aircraft also comprises structural parts that are made of composite material such as the cross-member 816 shown in the same figure.

The term "composite material" is used herein to mean a weld of at least two non-miscible materials that nevertheless presents strong capacity for adhesion. A composite material comprises a framework or reinforcement that provides it with mechanical strength, and also a protective matrix. Specifically, the matrix may be of plastics material and the reinforcement may be made of carbon fibers. The material here is thus a carbon fiber reinforced plastics material. The rail 814 rests on the cross-member 816, extending perpendicularly thereto and being fastened thereto by means of a structural junction element 818.

Figure 7:
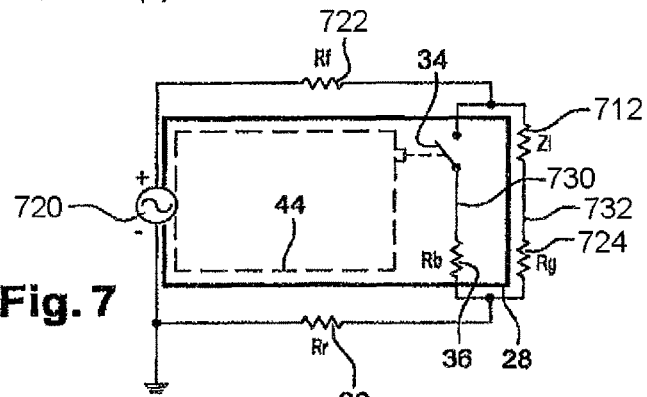
FIG. 7 is an electrical circuit diagram showing how equipment is connected on board the FIG. 1 airplane.

FIG. 7 is an electrical circuit diagram showing the way the equipment 712 is connected to an electricity generator 720 on board the airplane 2. Here the generator is of the single-phase type. The equipment 712, represented in the diagram by its impedance ZI is connected to the positive terminal of the generator by means of a conductor such as a cable 722 that presents a resistance Rf. It is also connected towards the negative terminal of the generator by a grounding conductor such as a cable 724 presenting a resistance Rg. This cable is itself connected to the ESN 26 of the airplane 2 that presents a resistance Rr in the return path for the operating current of the equipment 712. These elements constitute the grounding circuit of the equipment 712 for returning operating currents, with the circuit being represented by bold lines referenced 28 in FIG. 7. This is the normal path followed by the electric current delivered by the generator 720 and powering the equipment 712 during normal operation thereof.

The figure shows a branch 730 that extends in parallel with the branch 732 comprising the equipment 712 and the cable 724 connected in series. The branch 730 illustrates the possibility of a short circuit that is symbolized by the switch 34 therein. In the event of such a short circuit, electric current coming from the positive terminal of the generator 720 passes, at least in part, via the branch 730, passes through the switch in the closed position, and follows a fault current circuit passing via an element 36 symbolized by a resistance Rb, and then via the ESN 26.

As shown in FIG. 8, the element 36 in this example is constituted by connecting the equipment 812 to the composite material part 816 by means of a cable 40 that is itself connected to a metal element 42 such as a plate that is fastened to the part 816. This fastening is performed using one or more metal members such as screws 43, each passing through the plate 42 and penetrating into the part 816.

Figure 9:
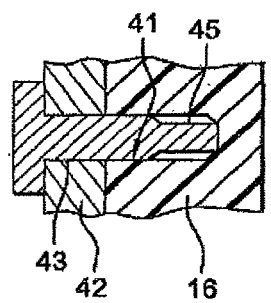
FIG. 9 is a section view of the connection on plane IX-IX of FIG. 8.

As shown in FIG. 9, each screw 43 is a tight fit with the part 816. For this purpose, the screw 43 presents specifically a smooth cylindrical segment along its shank that is in contact with the part 816. Here the thread 45 thus extends over only a fraction of the shank of the screw, along its distal end segment. The screw is received in a calibrated bore 41 in the part 816 that is prepared prior to inserting the screw. Specifically, the diameter v of the screw 43 and the diameter e of the bore satisfy the following equation:

$$(v-e)/v \geq 0.0025$$

Such a tight fit enables the face of the shank of the screw to be pressed against the composite face of the bore. Radial pressure is thus established between the screw and the part so as to achieve contact pressure between the screw and the bore that exceeds 100 megapascals (MPa). This threshold serves to ensure that the electrical contact resistance between the screw and the part is substantially constant and at a minimum. The value of 0.0025 makes it possible to ensure that the contact resistance is negligible. Even better results are obtained if the contact resistance is reduced even more by using a minimum value equal to 0.0030 or even 0.0035. Naturally, it is preferable in contrast to limit the ratio (v−e)/v so that it does not exceed 0.0083, for example, so as to avoid exceeding the mechanical strength of the plastics material.

The equipment 812 is thus electrically connected to the part 816, which part is connected via the rail 814 to the ESN 26 of the airplane. The element 36 shown in the circuit of FIG. 7 is thus formed in this example by the cable 40, the plate 42, the screw 43, and the portion of the part 816 that conveys the fault current, if any.

Thus, in the presence of a short circuit symbolized by closing the switch 34, the current no longer follows the branch 732, but rather the branch 730. The fault current is thus carried by a circuit that passes in particular via the composite material part 816. This fault current circuit 44 is represented by dashed lines in FIG. 7.

Figure 10:
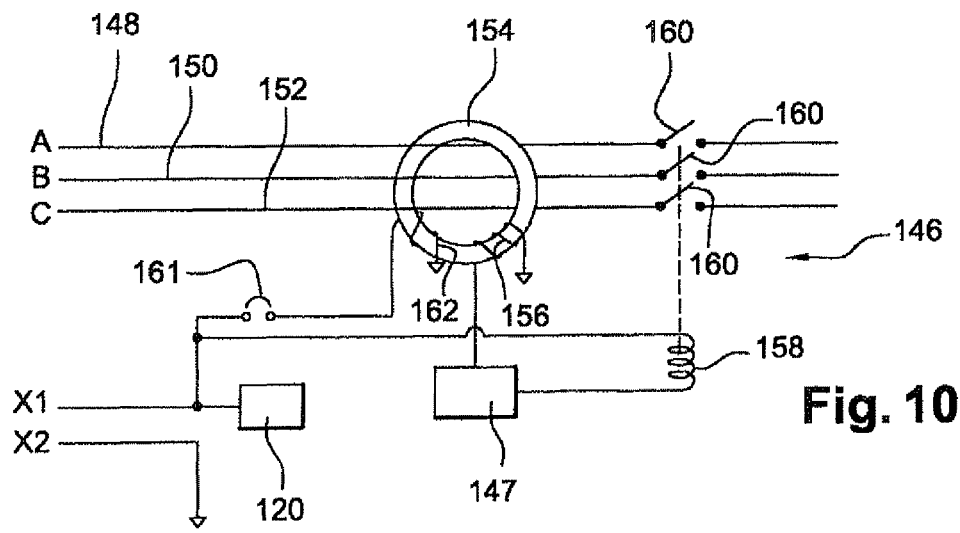
FIG. 10 is an electrical circuit diagram showing a variant of the principle of a monitoring device.
Figure 11:
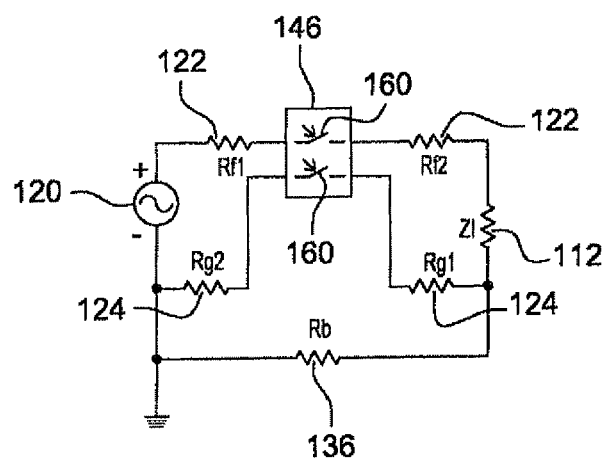
FIG. 11 is an electrical circuit diagram of the connection of equipment incorporating said monitoring device.

In the variant shown in FIGS. 10 and 11, it is possible to envisage protecting the equipment 112 against fault currents by means of a monitoring device 146. The structure and the operation of such a device are shown in FIG. 10 in the context of an electrical power supply of the three-phase type. The principle nevertheless remains similar in the presence of a single-phase power supply. The three strands A, B, and C of an on-board three-phase power supply thus include three branches 148, 150, and 152. The device 146 comprises a torus 154 through which these three branches pass. A single-phase power supply 120 is shown with its positive terminal represented by a branch x1 while ground is shown as being represented by a branch x2. The device 146 includes a central control module 147, a winding 156 around the torus 154 and connected both to the module 147 and to ground, and a coil 158 connected to the power supply 120 and to the module 147. When powered, the coil actuates switches 160 that are located in each of the branches A, B, and C, enabling current flow in each of them to be interrupted.

Under normal operating conditions, which here is a balanced three-phase mode, the sum of the currents flowing in the phases A, B, and C is zero. Consequently, no magnetic flux flows in the torus 154. The switches 160 thus remain closed.

In the event of a fault, e.g. when a short circuit appears in the load powered by this three-phase power supply, the sum of the currents in the phases A, B, and C is no longer zero such that magnetic flux appears in the torus 154. This flux induces current in the winding 156, which current is transmitted to the module 147. The module then causes the coil 158 to be powered so as to open the switches 160, thereby preventing current from flowing in the branches A, B, and C.

The device 146 includes a test branch extending in parallel with the branch powering the coil 158. The test branch is connected to the branch x1 of the power supply 120 and includes a button 161 and a winding 162 around the torus 154. This winding is also connected to ground. When the button 161 is pressed, the winding 162 is powered from the generator 120, thereby causing magnetic flux to appear in the torus 154 and inducing current in the winding 156. As before, the flow of current in each of the branches A, B, and C is interrupted.

FIG. 11 shows the principle for connecting the equipment 112. It can thus be seen that the equipment is powered by the positive terminal of the generator 120 via a cable 122 having resistances Rf1 and Rf2.

In normal operation, current is carried to the ground of the airplane via a cable 124 presenting resistances Rg1 and Rg2. The monitoring device 146 is mounted on each of these cables 122 and 124. In the presence of a fault current, the current no longer passes via the cable 122, but passes via the fault circuit including the element 136 of resistance Rb.

The monitoring device 146 includes a respective switch 160 for each of the cables 122 and 124. In normal operation, both switches are closed so that the cables 122 and 124 pass electricity. In the event of a fault, electricity passes via the fault circuit of the cable 136, thereby generating unbalance in the currents conveyed by the cables 122 and 124. Consequently, the monitoring device 146 causes the two switches 160 to open, thereby interrupting any connection between the equipment 112 and the generator. The equipment 112 is thus protected.

The principle shown in FIG. 10 is applicable regardless of the mode of the power supply, i.e. whether it is an alternating current (AC) power supply or a direct current (DC) power supply.

The dimensioning of the various elements and in particular the capacity of the switches 160 are calculated as a function of the impedance Rb, which is itself associated with the quality of the contact resistance between the screws 43 and the part 816 and with the resistance of said part, which magnitude is also important for injecting electric current into the composite material.

Similarly, the arrangement should be capable of enabling a relatively high level of current to flow continuously.

By way of example, the device 146 may be positioned at the contactors of the power supply routes of the pieces of equipment making up the equipment 112. However such an embodiment suffers from the drawback of interrupting electrical power supply to all of the pieces of equipment connected to a given contactor even though only one of the pieces of equipment presents a fault current.

It is therefore preferable to implement the functions of the device 146 for each piece of equipment on its own. It is then possible to provide a monitoring device that is dedicated to each piece of equipment in order to protect it from overcurrents. By way of example, the monitoring device may be in the form of a solid state power contactor.

It can be understood that each of the pieces of equipment in the airplane may be connected to a part 816 that is distinct from the part to which at least one other piece of equipment of the airplane is connected, or indeed that is dedicated to a single piece of equipment, these pieces of equipment also using the same ESN.

It can be seen that this application avoids the need to complicate the network for returning fault currents and the need to make it any heavier.

Naturally, numerous modifications may be made to the invention without going beyond its ambit.

It is possible to combine measurements that are not all taken on the same part.

Knowing that the contact resistance is eliminated by combining the equations, it is possible to perform the same operations with a force that is less than the above-mentioned threshold.

The housings 32 need not necessarily be in alignment.

The invention may be used to obtain magnitudes other than a resistance value, for example to obtain a conductance value or an impedance value.

What is claimed is:

1. A method of electrically characterizing a composite material for manufacturing an aircraft, the method comprising:
compressing first and second spacers against a first test piece made of the composite material to be electrically characterized to form: (i) a first assembly; and (ii) an interference fit between at least one of the first and second spacers and an orifice in the first test piece established by insertion of the at least one of the first and second spacers into the orifice;
successively compressing, while a location of one of the first and second spacers is unchanged, the first and second spacers against a second test piece to form: (i) a second assembly; and (ii) an interference fit between at least one of the first and second spacers and an orifice in the second test piece established by insertion of the at least one of the first and second spacers into the orifice, the first and second test pieces made of the same composite material, the unchanged location shared by the first and second test pieces;
determining an electrical resistance value of each of the first and second assemblies; and
deducing from the electrical resistance values of the first and second assemblies an electrical resistance value of the composite material of the first and second test pieces.

2. The method according to the claim 1, wherein the compression is performed in such a manner that the at least one test piece is subjected to a contact pressure exceeding a predetermined threshold.

3. The method according to claim 1, wherein the at least one of the spacers has a diameter (c) greater than a diameter (e) of the orifice, the diameter (c) and the diameter (e) satisfying the following equation:

$$(c-e)/c \geq 0.0025.$$

4. The method according to claim 1, wherein the compression is performed on at least two test pieces made of the same composite material, and the compression is performed in succession on the at least two test pieces while the location of one of the spacers unchanged.

5. The method according to claim 4, wherein the at least two test pieces form portions of a single part.

6. The method according to claim 5, wherein three spacers are arranged on the part at locations that are mutually in alignment.

7. A method of manufacturing an aircraft, comprising:
manufacturing the aircraft with a composite material electrically characterized by a method according to claim 1 and by taking account of the electrical resistance value of the material as obtained by the method of claim 1;

connecting electrical equipment of the aircraft to a part made of the composite material; and arranging the aircraft in such a manner that a fault current circuit for the equipment passes via the part.

8. An installation for electrically characterizing a composite material for use in manufacturing an aircraft, the installation comprising:

first and second spacers;

a device configured to compress the first and second spacers against a first test piece made of the composite material to be electrically characterized to form: (i) a first assembly; and (ii) an interference fit between at least one of the first and second spacers and an orifice in the first test piece established by insertion one of the first and second spacers into the orifice in the first test piece, the device further configured to compress, while a location of one of the first and second spacers is unchanged, the first and second spacers against a second test piece to form: (ii) a second assembly; and (ii) an interference fit between at least one of the first and second spacers and an orifice in the second test piece, the first and second test pieces made of the same composite material, the unchanged location shared by the first and second test pieces; and a device that determines an electrical resistance value of each of the first and second assemblies.

* * * * *